Figure 2:
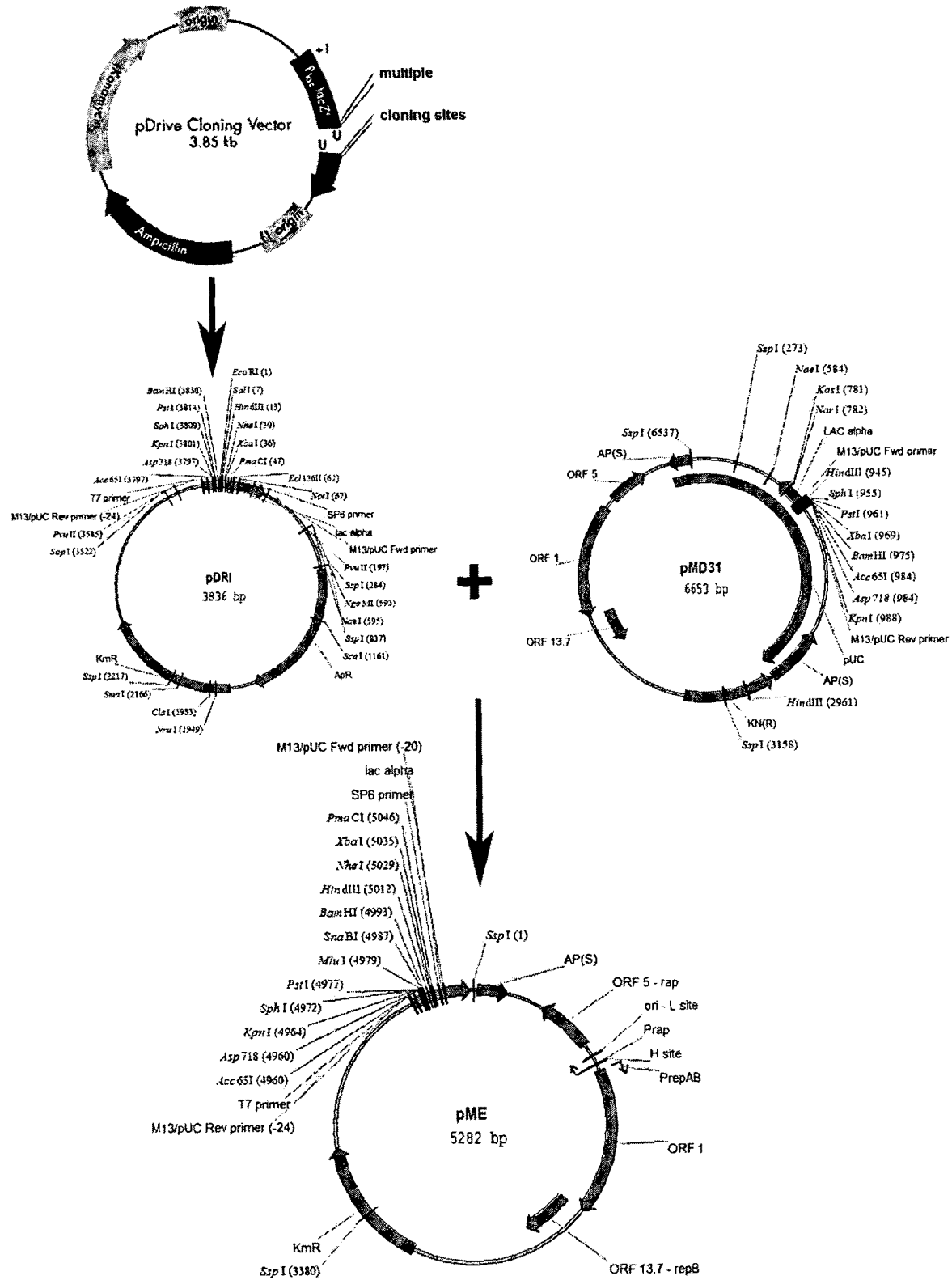
Figure 3:
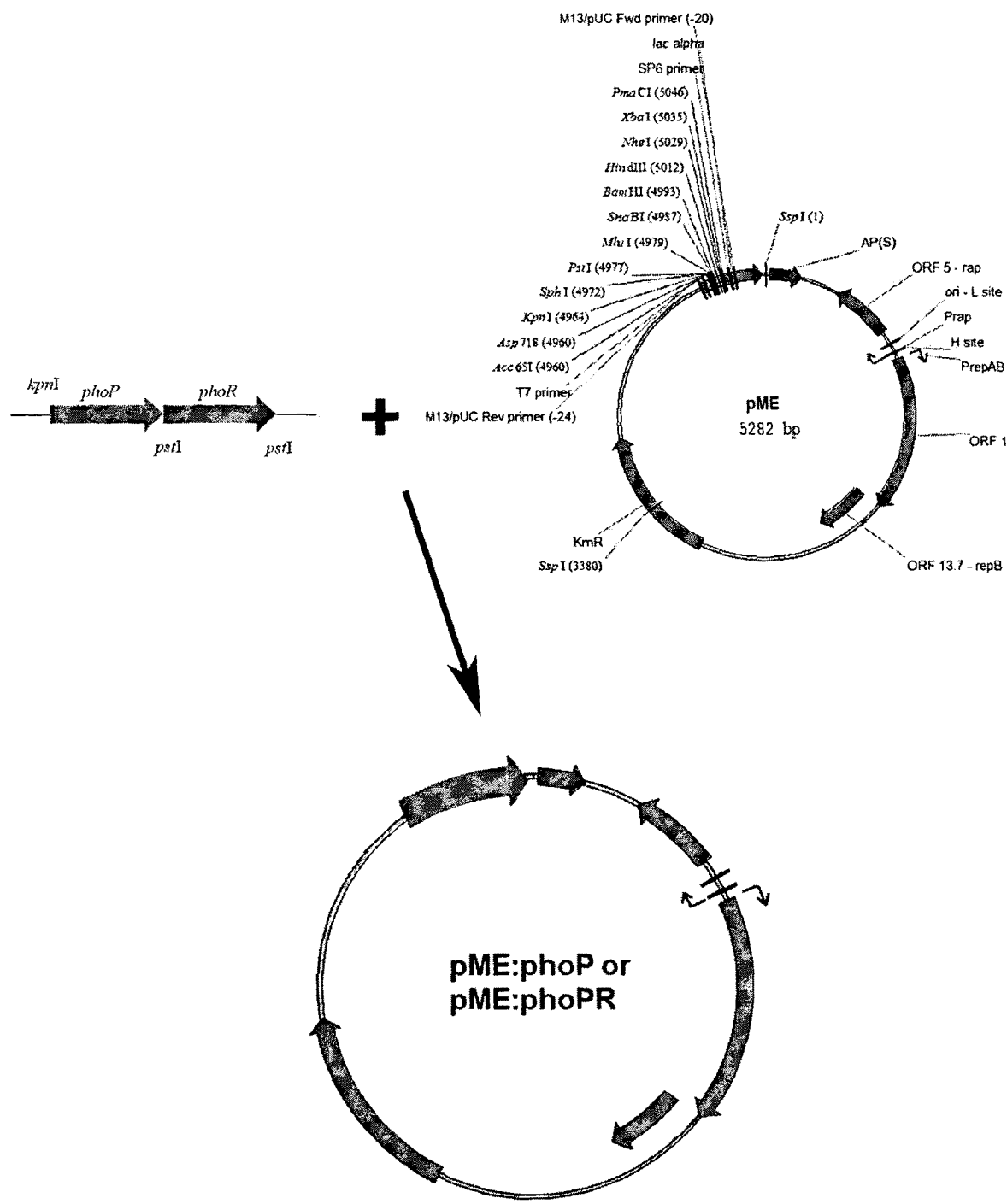

US011717565B2

(12) United States Patent
Liu

(10) Patent No.: US 11,717,565 B2
(45) Date of Patent: Aug. 8, 2023

(54) **RECOMBINANT BCG OVEREXPRESSING *PHOP-PHOR***

(71) Applicant: Chengdu Anyong Dingye Biotechnology Co., Ltd., Chengdu (CN)

(72) Inventor: Jun Liu, Oakville (CA)

(73) Assignees: CHENGDU ANYONG DINGYE BIOTECHNOLOGY CO., LTD., Chengdu (CN); LTD., Chengdu (CN)

( * ) Notice: Subject to any disclaimer, the term of this patent is extended or adjusted under 35 U.S.C. 154(b) by 0 days.

(21) Appl. No.: 16/500,934

(22) PCT Filed: Apr. 7, 2017

(86) PCT No.: PCT/CN2017/079665
§ 371 (c)(1),
(2) Date: Oct. 4, 2019

(87) PCT Pub. No.: WO2018/184188
PCT Pub. Date: Oct. 11, 2018

(65) Prior Publication Data

US 2020/0254080 A1 Aug. 13, 2020

(51) Int. Cl.
*A61K 39/04* (2006.01)
*A61P 31/06* (2006.01)
*C12N 1/20* (2006.01)
*C12R 1/32* (2006.01)

(52) U.S. Cl.
CPC .............. *A61K 39/04* (2013.01); *A61P 31/06* (2018.01); *C12N 1/20* (2013.01); *C12N 1/205* (2021.05); *C12R 2001/32* (2021.05)

(58) Field of Classification Search
None
See application file for complete search history.

(56) References Cited

U.S. PATENT DOCUMENTS

2004/0120962 A1 6/2004 Curtiss et al.

FOREIGN PATENT DOCUMENTS

RU 2443773 C2 2/2012
WO WO-2011/130878 4/2010
WO WO-2011130878 A1 * 10/2011 .............. A61P 31/06

OTHER PUBLICATIONS

Broset et al. mBio. vol. 6, issue 5, Sep./Oct. 2015. (Year: 2015).*
Leung et al. BMC Genomic 2008, No. 413, pp. 1-12 a (Year: 2008).*
Database Unitprot Accession, No. A0A0R3M2A3 Sep. 2015 (Year: 2015).*
Leung et al., Novel genome polymorphisms in BCG vaccine strains and impact on efficacy, BMC Genomics, 9:1 (Sep. 2008).
Database Uniprot Accession No. A0A0H3M2A3, last modifed Sep. 16, 2015.
Japanese Patent Application No. 2019-538338, Office Action, dated Sep. 1, 2020.
Broset et al., Evolutionary landscape of the *Mycobacterium tuberculosis* complex from the viewpoint of PhoPR: implications for virulence regulation and application to vaccine development, MBio, 6(5):e01289-15 (Oct. 2015).
Cimino et al., Identification of DNA binding motifs of the *Mycobacterium tuberculosis* PhoP/PhoR two-component signal transduction system, PLoS One, 7(8):e42876 (2012).
GenBank Accession No. 5ED4_A, Chain A, Structure of a Phop-dna complex, Apr. 28, 016.
GenBank Accession No. WP_015456166.1, DNA-binding response regulator [*Mycobacterium tuberculosis*], Oct. 2, 2015.
GenBank Accession No. WP_051989415.1, DNA-binding response regulator [*Mycobacterium bovis*], Oct. 3, 2015.
GenBank Accession No. WP_053904767.1, ATP-binding protein [*Mycobacterium bovis*], Sep. 20, 2015.
International Application No. PCT/CN2017/079665, International Search Report and Written Opinion, dated Jan. 3, 2018.
Wu et al., PhoP-PhoR two-component signal transduction systems in pathogenesis of *Mycobacterium tuberculosis*, Chin. J. Zoonoses, 10(30):1062-5 (Dec. 2014).
Goude et al., Electroporation of Mycobacteria, IN: Parish et al. (eds.), Mycobacteria Protocols. Methods in Molecular Biology, Totowa, NJ: Humana Press, vol. 465, pp. 203-215, see p. 203 abstract (2008).
Singer et al., Genes and Genomes in 2 volumes, vol. 1, Moscow, Russia: Mir Publishers, Figures see p. 33 (1998).
Pakula et al., Genetic analysis of protein stability and function, Annu. Rev. Genet., 23:289-310 (1989).
Kumar et al., EspR-dependent ESAT-6 Protein Secretion of *Mycobacterium tuberculosis* Requires the Presence of Virulence Regulator PhoP, J. Biol. Chem., 291(36):19018-30 (2016).
Russian Patent Application No. 2019130941, Office Action, dated Sep. 21, 2020.

* cited by examiner

*Primary Examiner* — Gary B Nickol
*Assistant Examiner* — Khatol S Shahnan Shah
(74) *Attorney, Agent, or Firm* — Marshall, Gerstein & Borun LLP

(57) ABSTRACT

Provided are a live recombinant *Mycobacterium bovis*-BCG strain and a tuberculosis (TB) vaccine or immunogenic composition comprising a nucleic acid capable of overexpression, the nucleic acid encoding PhoP and PhoR proteins. A method for treatment or prophylaxis of a mammal against challenge by *Mycobacterium tuberculosis* or *Mycobacterium bovis* using the strain is also provided.

9 Claims, 8 Drawing Sheets

Specification includes a Sequence Listing.

Figure 1 a. SEQ ID NO:1

```
         10         20         30         40         50         60
MRKGVDLVTA GTPGENTTPE ARVLVVDDEA NIVELLSVSL KFQGFEVYTA TNGAQALDRA
         70         80         90        100        110        120
RETRPDAVIL DVMMPGMDGF GVLRRLRADG IDAPALFLTA RDSLQDKIAG LTLGGDDYVT
        130        140        150        160        170        180
KPFSLEEVVA RLRVILRRAG KGNKEPRNVR LTFADIELDE ETHEVWKAGQ PVSLSPTEFT
        190        200        210        220        230        240
LLRYFVINAG TVLSKPKILD HVWRYDFGGD VNVVESYVSY LRRKIDTGEK RLLHTLRGVG

YVLREPR
``` b. SEQ ID NO:2

```
  1 - atg cgg aaa ggg gtt gat ctc gtg acg gcg
 31 - gga acc cca ggc gaa aac aca ccg gag
 61 - gct cgt gtc ctc gtg gtc gat gat gag gcc
 91 - aac atc gtt gaa ctg ctg tcg gtg agc ctc
121 - aag ttc cag ggc ttt gaa gtc tac acc gcg
151 - acc aac ggg gca cag gcg ctg gat cgg gcc
181 - cgg gaa acc cgg ccg gac gcg gtg atc ctc
211 - gat gtg atg atg ccc ggg atg gac ggc ttt
241 - ggg gtg ctg cgc cgg ctg cgc gcc gac ggc
271 - atc gat gcc ccg gcg ttg ttc ctg acg gcc
301 - cgt gac tcg cta cag gac aag atc gcg ggt
331 - ctg acc ctg ggt ggt gac gac tat gtg aca
361 - aag ccc ttc agt ttg gag gag gtc gtg gcc
391 - agg ctg cgg gtc atc ctg cga cgc gcg ggc
421 - aag ggc aac aag gaa cca cgt aat gtt cga
451 - ctg acg ttc gcc gat atc gag ctc gac gag
481 - gag acc cac gaa gtg tgg aag gcg ggc caa
511 - ccg gtg tcg ctg tcg ccc acc gaa ttc acc
541 - ctg ctg cgc tat ttc gtg atc aac gcg ggc
571 - acc gtg ctg agc aag cct aag att ctc gac
601 - cac gtt tgg cgc tac gac ttc ggt ggt gat
631 - gtc aac gtc gtc gag tcc tac gtg tcg tat
661 - ctg cgc cgc aag atc gac act ggg gag aag
691 - cgg ctg ctg cac acg ctg cgc ggg gtg ggc
721 - tac gta ctg cgg gag cct cga tga
``` c. SEQ ID NO:3

```
         10         20         30         40         50         60
MARHLRGRLP LRVRLVAATL ILVATGLVAS GIAVTSMLQH RLTSRIDRVL LEEAQIWAQI
         70         80         90        100        110        120
TLPLAPDPYP IHNPDRPPSR FYVRVISPDG QSYTALNDNT AIPAVPANND VGRHPTTLPS
        130        140        150        160        170        180
IGGSKTLWRA VSVRASDGYL TTVAIDLADV RSTVRSLVLL QVGIGSAVLV VLGVAGYAVV
        190        200        210        220        230        240
RRSLRPLAEF EQTAAAIGAG QLDRRVPQWH PRTEVGRLSL ALNGMLAQIQ RAVASAESSA
        250        260        270        280        290        300
EKARDSEDRM RQFITDASHE LRTPLTTIRG FAELYRQGAA RDVGMLLSRI ESEASRMGLL
        310        320        330        340        350        360
VDDLLLLARL DAHRPLELCR VDLLALASDA AHDARAMDPK RRITLEVLDG PGTPEVLGDE
        370        380        390        400        410        420
```

Figure 1 (continued)

```
SRLRQVLRNL VANAIQHTPE SADVTVRVGT EGDDAILEVA DDGPGMSQED ALRVFERFYR
    430        440        450        460        470        480
ADSSRARASG GTGLGLSIVD SLVAAHGGAV TVTTALGEGC CFRVSLPRVS DVDQLSLTPV

VPGPP
``` d. SEQ ID NO:4

```
   1 - atg gcc aga cac ctt cga gga agg ctg ccc
  31 - cta cgg gta cgc ctg gtc gca gcc acg ctg
  61 - atc ctg gtg gcc act gga ctt gtg gcc tcg
  91 - ggg atc gcg gtc acc tcg atg ttg cag cac
 121 - cgg ctg acc agc cgg atc gat cgg gtg ttg
 151 - ctc gag gaa gcc caa atc tgg gcg cag atc
 181 - acg ctg ccc ttg gcg ccg gac ccc tac cct
 211 - att cat aac ccc gat cgg ccg ccg tcg agg
 241 - ttc tac gtt cgg gtg atc agc ccc gac ggc
 271 - cag agc tat acg gca ctc aac gac aac act
 301 - gcc ata ccg gcg gtg ccc gcc aac aat gat
 331 - gtc ggc cgg cac ccg acg acg ctg cca tcg
 361 - atc ggc gga tcc aag act tta tgg cgc gcg
 391 - gtc tcg gtg cgc gcg tcg gat ggc tac ttg
 421 - acc acc gtc gcc att gat ctg gcc gac gtc
 451 - cgg agc acc gtg cgg tca ctg gtg ctg ttg
 481 - cag gtc ggc ata ggc agt gcg gtg ctg gtt
 511 - gtc ctc ggg gtg gcg ggc tac gct gtg gtt
 541 - cgc cgc agc ctg cgg ccg ctg gca gaa ttc
 571 - gag cag acg gcc gcg gcg atc ggc gcg ggg
 601 - cag ctg gat cgc cgg gtc ccg cag tgg cat
 631 - ccg cga act gag gtc ggc cgg ctt tcg ttg
 661 - gcg ctc aac gga atg ctg gca caa att cag
 691 - cgg gcg gtg gcg tcc gcg gaa tct tcc gcc
 721 - gaa aag gcc cgg gat tca gag gac cgg atg
 751 - cga cag ttc atc acc gac gcc agc cat gaa
 781 - ctg cgt acc ccg ttg acc act atc cgc ggc
 811 - ttc gcg gag ctg tac cga caa gga gcc gcc
 841 - cgc gac gtg ggc atg ctg ctg tcg cgg att
 871 - gag agc gaa gcg agc cgg atg ggc ctg ctg
 901 - gtg gac gat ttg ctg ctg ctt gcc cgg cta
 931 - gat gcg cac cgg ccg ttg gaa ctg tgc cgg
 961 - gtg gac ctg ctg gcg ctg gcc agt gat gcc
 991 - gcg cac gac gcg cgg gcg atg gac ccc aaa
1021 - cgc agg atc acc ctg gag gtc ctt gac ggc
1051 - ccc ggc acc ccg gag gtc ctc ggc gac gaa
1081 - tcg cgg ctt cgg cag gtg ctg cgc aat ctc
1111 - gtt gca aat gcc ata cag cac acc ccg gaa
1141 - agc gcc gac gtc acc gtg cga gtc ggc acc
1171 - gag ggc gac gac gcc atc ctc gag gtc gcc
1201 - gat gac ggt ccg ggc atg agt cag gag gat
1231 - gcg ctg cgg gtg ttc gag cgg ttc tat cgc
1261 - gcc gac tcg tcg cgg gcg cgc gcc agc ggc
1291 - ggg acc gga ctg ggg ttg tcg atc gtc gac
1321 - tct ttg gtg gcg gcc cat ggc gga gcg gtc
1351 - acc gtg acg acc gcg ctc ggg gag ggt tgc
1381 - tgc ttt cgt gtc tcg ctg ccg cgc gtc agt
1411 - gac gtg gac cag ctg agc ctc acg cca gtt
1441 - gtg cca ggg ccg ccc tga
```

RECOMBINANT BCG OVEREXPRESSING PHOP-PHOR

INCORPORATION BY REFERENCE OF MATERIAL SUBMITTED ELECTRONICALLY

This application contains, as a separate part of disclosure, a sequence listing in computer-readable form (filename: 54507_SeqListing.txt; 10,563 bytes; created: Mar. 11, 2020) which is incorporated by reference in its entirety.

FIELD OF THE INVENTION

This invention relates to tuberculosis (TB) vaccines. In particular, the invention provides a recombinant BCG that overexpresses the phoP-phoR two-component regulatory system and confers enhanced protection against tuberculosis.

BACKGROUND OF THE INVENTION

Tuberculosis (TB), caused by *Mycobacterium tuberculosis* (*M. tb*), ranks alongside HIV/AIDS as a major cause of mortality by infectious diseases worldwide. In 2014, TB caused 1.5 million deaths and 9.6 million new infections. The lack of a protective vaccine, the emergence of drug-resistant *M. tb* strains, and the high rate of *M. tb*/HIV coinfection continue to fuel the TB epidemic. Bacille Calmette-Guérin (BCG) is the only licenced TB vaccine and although it is effective against disseminated forms of TB in children[1,2], BCG has limited protection against pulmonary TB in adults, the most common and contagious form of the disease. Clinical studies have shown variable efficacies ranging from 0 to 80%[3-5].

One hypothesis to explain the variable efficacy of BCG concerns the heterogeneity of BCG strains[6]. BCG was derived from a virulent strain of *Mycobacterium bovis* through in vitro passaging from 1908-1921. Subsequent worldwide distribution and continuous passaging until the 1960s resulted in a number of BCG substrains. Genetic differences among BCG strains including deletions and duplications of genomic regions and single nucleotide polymorphisms (SNPs) have been well documented[7-12]. Whether these differences affect BCG effectiveness against TB is a matter of debate[6,13], and currently there are insufficient data to recommend one particular strain because of the paucity of clinical trials directly comparing multiple BCG strains[14].

Current strategies to improve TB vaccines include the development of subunit and live attenuated vaccines[15,16]. However, none of the subunit vaccines have proved to be superior to BCG in animal models. The lack of protective efficacy of MVA85A, the most advanced subunit vaccine, in BCG-vaccinated infants in a recent clinical trial[17] further emphasizes the importance of live vaccine research[18]. A number of approaches have been explored to develop live vaccines including the generation of recombinant BCG and attenuated *M. tb* strains. Of these, only a few have proven to be superior to BCG in animal models including the three live vaccines (rBCG30, VPM1002, and MTBVAC) that have entered clinical trials[16]. rBCG30 is a recombinant BCG-Tice strain that overexpresses antigen Ag85B. rBCG30-vaccination of guinea pigs followed by *M. tb* challenge resulted in a reduction of the bacterial burden by 0.5-1.0 $\log_{10}$ and prolonged survival compared to those immunized with the parental BCG[19,20]. However, this effect was specific to BCG-Tice since overexpression of Ag85B in BCG-Connaught did not improve protection[20]. VPM1002 is a recombinant BCG that expresses listeriolysin of *Listeria monocytogenes*. The rationale behind this vaccine was the notion that listeriolysin could facilitate phagosomal escape of BCG into the cytosol of macrophages, thereby increasing antigen presentation[21]. BALB/c mice vaccinated with VPM1002 showed a reduction in *M. tb* burden by 0.5-1.0 $\log_{10}$ compared to the parental strain[21,22]; however, this improvement in protection was not observed in the guinea pig model[23]. A phoP deletion mutant of *M. tb* was evaluated as a vaccine candidate with the reasoning that attenuated *M. tb* may share more antigens with clinical strains of *M. tb* than BCG[24]. *M. tb* ΔphoP provided similar protection as BCG in mice but better protection in guinea pigs against *M. tb* challenge[24,25]. To ensure safety, fadD26 was deleted to further attenuate the strain (MTBVAC), which showed a comparable safety profile to BCG-Pasteur or BCG-Danish in SCID mice[26].

SUMMARY OF THE INVENTION

The present invention provides tuberculosis vaccines comprising a recombinant *Mycobacterium* strain that overexpresses phoP-phoR, a two-component regulatory system. The immunogenicity of current BCG vaccine strains is not sufficient to induce the optimal protection in host against tuberculosis. In contrast, a genetically engineered BCG strain of present invention that overexpresses phoP-phoR is more immunogenic and provides better protection against tuberculosis. Any genetically engineered *Mycobacterium* that overproduces phoP-phoR at a level sufficient to cause a 2-(or more) fold induction of the PhoP-PhoR regulated genes or proteins may be advantageously used in the practice of this invention. When the recombinant *Mycobacterium* of the invention is administered to a mammalian host, the production of IFN-γ by CD4⁺ T cells is increased in the host, and this recombinant *Mycobacterium* provides protection against tuberculosis.

There have been over a dozen studies comparing the immune response induced by different BCG strains in humans[14,27]. However, only two or three BCG strains were included in the majority of these studies. Differences in study design such as the choice of BCG strains, age at immunization, and population size have led to inconclusive results[14]. Nonetheless, the largest of these studies, which was led by the WHO in the 1970s, compared 11 BCG strains in children[28]. BCG-Prague was found to be an outlier, exhibiting lower tuberculin reactivity than the other BCG strains, including BCG-Danish, -Pasteur, -Glaxo, -Japan, -Russia, and -Moreau[28,29]. Concern over its low immunogenicity resulted in its replacement by BCG-Russia in Czechoslovakia in 1981, after nearly 30 years of use[30]. Reasons for the low tuberculin reactivity of BCG-Prague remain unknown. However, the inventor found that phoP in BCG-Prague is pseudogene, containing a 1-bp insertion that disrupts the C-terminal DNA-binding domain[9]. This mutation is specific to BCG-Prague since all other BCG strains contain a wild type (WT) phoP. PhoP is a response regulator of the PhoP-PhoR two-component system and positively regulates more than 40 genes in *M. tb*, including two T cell antigens (Ag85A, PPE18) that have been used to construct subunit vaccines[16,31]. As such, the inventor hypothesized that the low immunogenicity of BCG-Prague is a result of phoP mutation[9], and that overexpression of phoP in BCG may provide an effective means to enhance immunogenicity and therefore protective efficacy. Consistently, the inventor showed in WO2011/130878A1 that complementation of BCG-Prague with WT phoP or overexpression of phoP in BCG-Japan increased IFN-γ production.

The present invention is based on the inventor's discovery that overexpression of phoP-phoR in BCG strain, such as BCG-Japan, enhanced its immunogenicity and protective efficacy, suggesting that this could be a generally applicable approach to improve BCG. It was demonstrated in the present invention that vaccination of C57BL/6 mice with the recombinant strain rBCG-Japan/PhoPR induced higher levels of IFN-γ production by CD4+ T cells than that with the parental BCG. Guinea pigs vaccinated with rBCG-Japan/PhoPR were better protected against challenge with *Mycobacterium tuberculosis*, showing significantly longer survival time, reduced bacterial burdens and less severe pathology, as compared with animals immunized with the parental BCG. Taken together, the recombinant BCG of present invention that overexpresses phoP-phoR has been confirmed to confer enhanced protection against tuberculosis than current BCG.

An exemplary amino acid sequence of PhoP is presented in FIG. 1A [SEQ ID NO:1] and an exemplary nucleotide sequence encoding the same is presented in FIG. 1B [SEQ ID NO:2]. An exemplary amino acid sequence of PhoR is presented in FIG. 1C [SEQ ID NO:3] and an exemplary nucleotide sequence encoding the same is presented in FIG. 1D [SEQ ID NO:4]. These sequences represent PhoP and PhoR from BCG-Pasteur, as presented in the genome sequence available at the Pasteur Institute's Website (http://genodb.pasteur.fr/cgi-bin/WebObjects/GenoList).

The present invention relates to a recombinant *Mycobacterium bovis* BCG, which overexpresses DNA encoding PhoP [SEQ ID NO:1; SEQ ID NO:2] and PhoR [SEQ ID NO:3; SEQ ID NO:4].

The present invention relates to a recombinant *Mycobacterium bovis* BCG comprising a nucleic acid capable of overexpression, the nucleic acid encoding PhoP [SEQ ID NO:1; SEQ ID NO:2] and PhoR [SEQ ID NO:3; SEQ ID NO:4].

In one embodiment, the recombinant *Mycobacterium bovis*-BCG strain is selected from the group consisting of *Mycobacterium bovis*-BCG-Russia, *Mycobacterium bovis*-BCG-Moreau, *Mycobacterium bovis*-BCG-Japan, *Mycobacterium bovis*-BCG-Sweden, *Mycobacterium bovis*-BCG-Birkhaug, *Mycobacterium bovis*-BCG-Prague, *Mycobacterium bovis*-BCG-Glaxo, *Mycobacterium bovis*-BCG-Denmark, *Mycobacterium bovis*-BCG-Tice, *Mycobacterium bovis*-BCG-Frappier, *Mycobacterium bovis*-BCG-Connaught, *Mycobacterium bovis*-BCG-Phipps, *Mycobacterium bovis*-BCG-Pasteur, and *Mycobacterium bovis*-BCG-China.

In addition, the recombinant mycobacteria of the invention need not be confined to strains of BCG. Those of skill in the art will recognize that other *Mycobacterium* strains may also be employed including attenuated strains of *M. tb.*

In yet another embodiment, the vaccine of the invention may be a subunit or DNA-vaccine. In some embodiments, the vaccine would be delivered via lung pathogens. For example, the DNA sequences coding for PhoP and PhoR could be harbored within the chromosome or extra chromosomal nucleic acid of a lung pathogen such as attenuated *Pseudomonas aeruginosa,* or other known attenuated fungi or viruses. Alternatively, the nucleic acid encoding PhoP and PhoR regulon could be delivered by other means known to those of skill in the art, e.g., via liposomes, adenoviral vectors, etc.

Another aspect of the invention is a pharmaceutical composition comprising a live recombinant *Mycobacterium bovis*-BCG strain comprising a nucleic acid capable of overexpression, the nucleic acid encoding PhoP [SEQ ID NO:1; SEQ ID NO:2] and PhoR [SEQ ID NO:3; SEQ ID NO:4].

In a further aspect of the invention there is a vaccine or immunogenic composition for treatment or prophylaxis of a mammal against challenge by mycobacteria comprising a live recombinant *Mycobacterium bovis*-BCG strain comprising a nucleic acid capable of overexpression, the nucleic acid encoding PhoP [SEQ ID NO:1; SEQ ID NO:2] and PhoR [SEQ ID NO:3; SEQ ID NO:4].

Another aspect of this invention relates to a method for treatment or prophylaxis of a mammal against challenge by *Mycobacterium tuberculosis* or *Mycobacterium bovis* comprising administering to the mammal a vaccine or immunogenic composition of the instant invention. In one embodiment the mammal is a cow. In another embodiment the mammal is a human. In yet another embodiment the vaccine or immunogenic composition is administered in the presence of an adjuvant.

A further aspect of the invention is a method for the treatment or prophylaxis of a mammal against cancer comprising administering to the mammal a vaccine or immunogenic composition of the current invention. In one embodiment the cancer is bladder cancer. In another embodiment the vaccine or immunogenic composition is administered in the presence of an adjuvant.

BRIEF DESCRIPTION OF THE DRAWINGS

FIG. 1 shows PhoP-PhoR sequences. (a) Amino acid sequence of PhoP of BCG-Pasteur; (b) DNA sequence of phoP of BCG-Pasteur. (c) Amino acid sequence of PhoR of BCG-Pasteur; (d) DNA sequence of phoR of BCG-Pasteur.

FIG. 2 shows the cloning vector pME.

FIG. 3 shows the constructed expression vectors for phoP and phoP-phoR.

FIG. 4 shows that rBCG-Japan/PhoPR induces more IFN-γ production by $CD4^+$ T cells than parental BCG.

FIG. 5 shows that rBCG-Japan/PhoPR prolongs the survival of guinea pigs infected with *M. tb.*

FIG. 6 shows that rBCG-Japan/PhoPR reduces the lung pathology of guinea pigs infected with *M. tb.*

FIG. 7 shows that rBCG-Japan/PhoPR is safe in SCID mice.

DETAILED DESCRIPTION OF THE INVENTION

Protection against TB requires cell-mediated immunity, which is not fully understood but involves multiple components including $CD4^+$ and $CD8^+$ T Cells[16,32,33]. BCG induces a T helper cell 1 (Th1) type response, mostly IFN-γ production by $CD4^+$ T cells[34]. Traditionally, immunogenicity of BCG was determined by measuring the tuberculin (PPD, purified protein derivatives of *M. tb*) sensitivity induced by the vaccine in children who were tuberculin-negative before vaccination[30]. While its use as a surrogate measure of protection has been questioned in recent years[35,36], tuberculin reactivity continues to be used as an in vivo assay for cell-mediated immune response and a marker for immunogenicity[19,37]. Supporting this, there is a strong association between tuberculin reactivity and PPD-specific IFN-γ levels in BCG-vaccinated infants[38]. Further, tuberculin reactivity and IFN-γ production were found to be non-redundant, complementary measures of anti-TB immunity in young people[39]. Studies in the 1970s found that BCG- Prague consistently exhibited significantly lower tuberculin reactivity in children and guinea pigs than the other 10 BCG strains tested[28,29]. Concern over its low immunogenicity resulted in its replacement by BCG-Russia in Czechoslovakia in 1981, after nearly 30 years of use[30].

Reasons for the reduced tuberculin reactivity of BCG-Prague are unknown. I hypothesized that the phoP mutation in BCG-Prague discovered in our previous study[9] contributes to its reduced immunogenicity.

To test this hypothesis, we first complemented BCG-Prague with an intact phoP gene and determined its effect on immunogenicity. The WT phoP gene from BCG-Pasteur was cloned into a multicopy shuttle vector pME and introduced into BCG-Prague (rBCG-Prague/PhoP). C57BL/6 mice were vaccinated with the recombinant BCG-Prague strains and the production of PPD-specific IFN-γ was measured by ELISA. Consistently, rBCG-Prague/PhoP induced higher levels of PPD-specific IFN-γ release in C57BL/6 mice, which was ~2.4 fold of that in mice immunized with the parental strain (FIG. 4a, $p<0.05$).

To test if overexpression of phoP can be used as a generally applicable method to improve BCG immunogenicity, we constructed a recombinant BCG overexpressing phoP in another BCG strain, BCG-Japan and generated rBCG-Japan/PhoP. PhoR is a histidine kinase that senses an unknown extracellular signal and phosphorylates PhoP[31]. Since BCG-Japan has an intact phoP phoR which is co-transcribed in its genome, we also generated rBCG-Japan/PhoPR, overexpressing both phoP and phoR to maintain the functional ratio of this two-component system.

Figure 4:
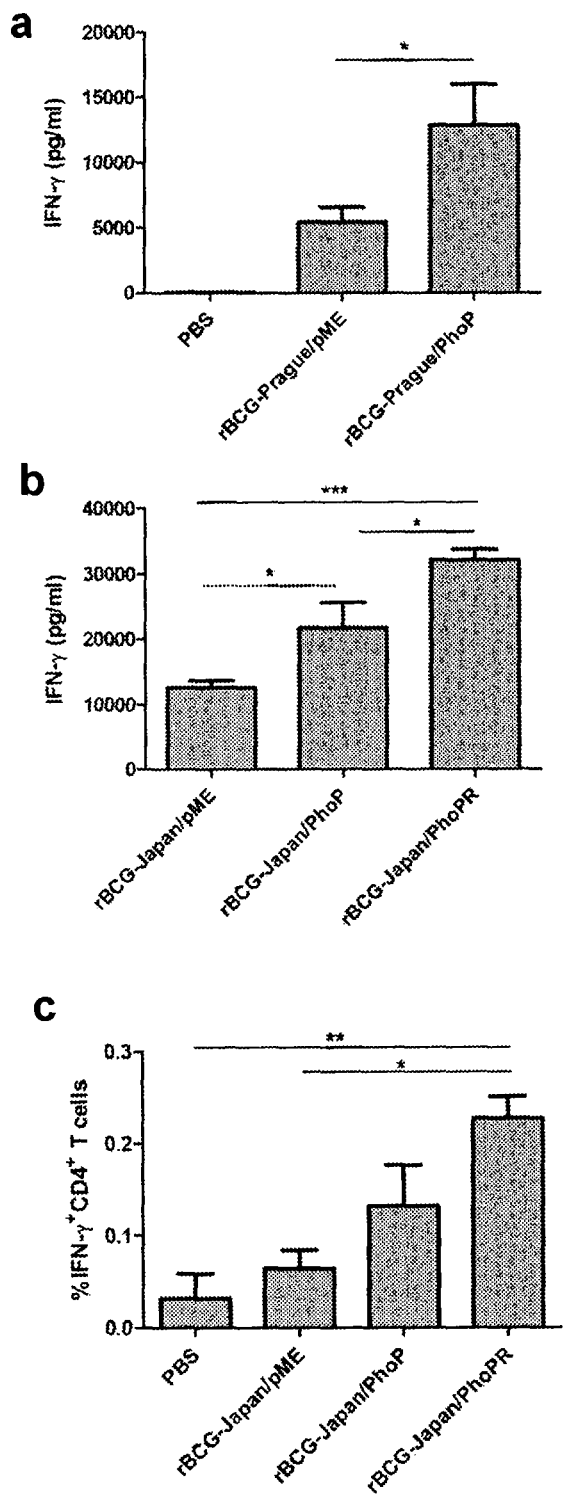

Consistent with the results obtained with BCG-Prague, both rBCG-Japan/PhoP and rBCG-Japan/PhoPR induced significantly higher levels of PPD-specific IFN-γ production in C57BL/6 mice than the parental strain (FIG. 4b). Interestingly, among the three strains, rBCG-Japan/PhoPR induced the highest level of IFN-γ.

To determine the source of IFN-γ induced by the recombinant BCG strains, we also performed intracellular cytokine staining and FACS analyses. We found that CD4$^+$ T cells were likely responsible for the enhanced IFN-γ release (FIG. 4c). The frequency of IFN-γ producing CD4$^+$ T cells in mice vaccinated with rBCG-Japan/PhoPR was ~3.5 fold of that in mice vaccinated with the parental strain, which is in agreement with the fold difference (~2.6 fold) of total IFN-γ production between these two groups (FIG. 4b, c).

In contrast, neither recombinant BCG-Japan strain induced a robust CD8$^+$ T cell response compared to the sham-immunized control. No significant induction of other cytokines (IL-2, TNF, IL-12, IL-4, IL-5, and IL-10) by the recombinant BCG-Japan strains was detected.

Taken together, these results suggest that the phoP mutation is partially responsible for the low immunogenicity of BCG-Prague. More importantly, overexpression of phoP-phoR in BCG-Japan further boosted IFN-γ production by CD4$^+$ T cells, suggesting that this could be a generally applicable approach to enhance the protective efficacy of BCG.

To examine if overexpression of phoP-phoR improves BCG-mediated protection against M. tb infection, we performed a long-term (10 months) guinea pig survival experiment. Guinea pigs (11 per group) were vaccinated with rBCG-Japan/PhoPR, the parental strain, or PBS and were challenged aerogenically with 1,000 CFU/lung of M. tb H37Rv 8 weeks post-vaccination. Guinea pigs were euthanized at the humane end-point and survival curves were plotted using a Kaplan-Meier analysis.

Figure 5:
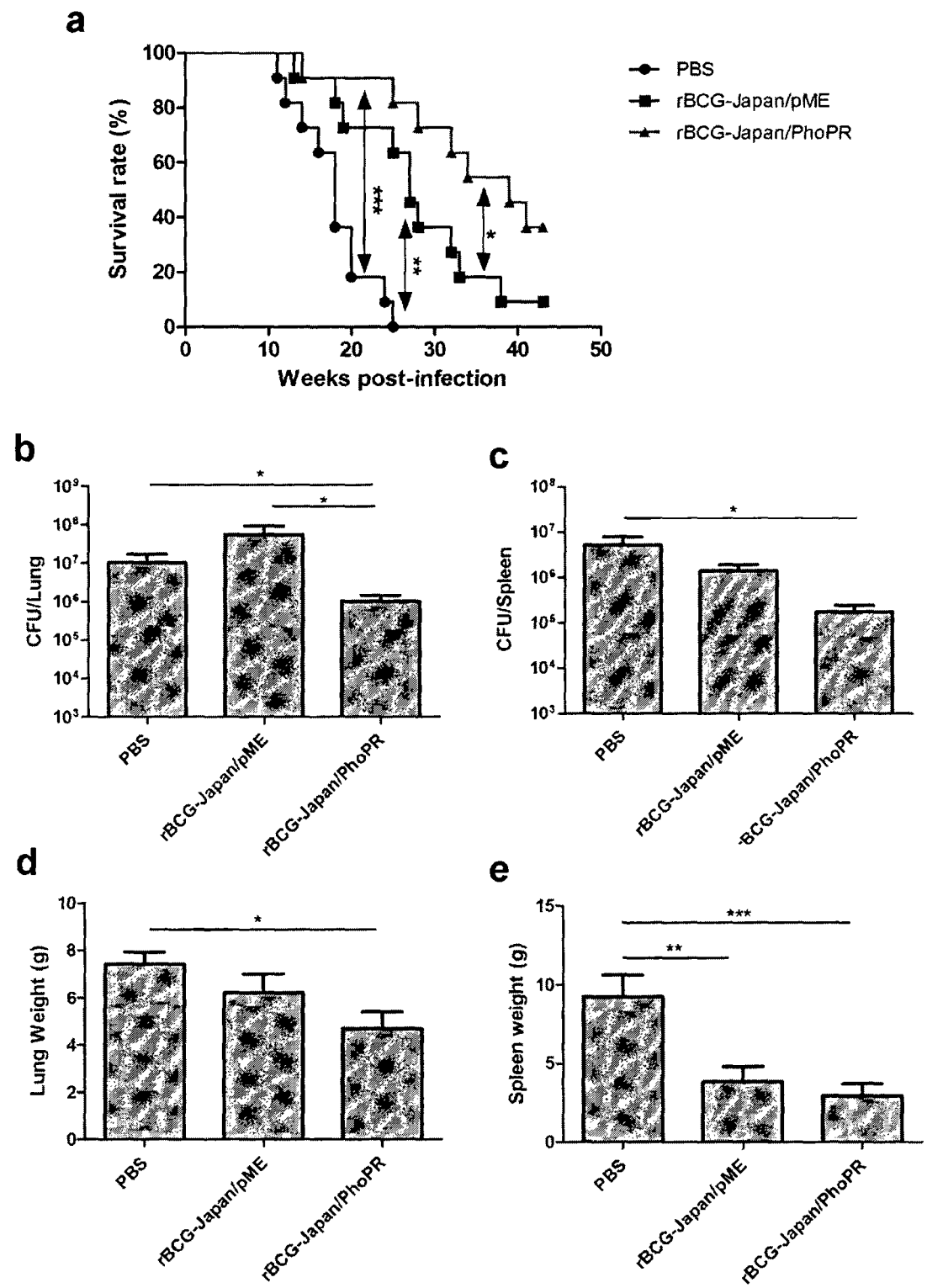

The median survival time for the PBS, the parental, and the rBCG-Japan/PhoPR groups were 18, 27, and 39 weeks, respectively (FIG. 5a). Log-rank analysis revealed that the rBCG-Japan/PhoPR group survived significantly longer than the parental BCG group ($p<0.05$) and the PBS group ($p<0.0001$). The parental group also survived significantly longer than the PBS group ($p<0.01$).

Compared to unvaccinated animals, the parental BCG prolonged the survival of guinea pigs by 9 weeks, while rBCG-Japan/PhoPR prolonged the survival of guinea pigs by 21 weeks (133% improvement over the parental group). At week 43 post-challenge when the experiment was terminated, only one guinea pig in the parental group survived compared to four animals in the rBCG-Japan/PhoPR group. All animals in the PBS group succumbed to infection by week 25.

The guinea pig lungs and spleen were further analyzed after the animals were euthanized at the humane or experimental endpoint. Similar to previous observation, the rBCG-Japan/PhoPR group had ~1.7 $\log_{10}$ lower M. tb counts in the lungs than the parental BCG group (FIG. 5b, $p<0.05$). The M. tb burden in the spleen of the rBCG-Japan/PhoPR group was also ~1.0 $\log_{10}$ lower than the parental BCG group and this difference is approaching significance ($p=0.066$). Consistently, the rBCG-Japan/PhoPR group had the lowest lung and spleen weights compared to the other two groups (FIG. 5d, e).

Figure 6:
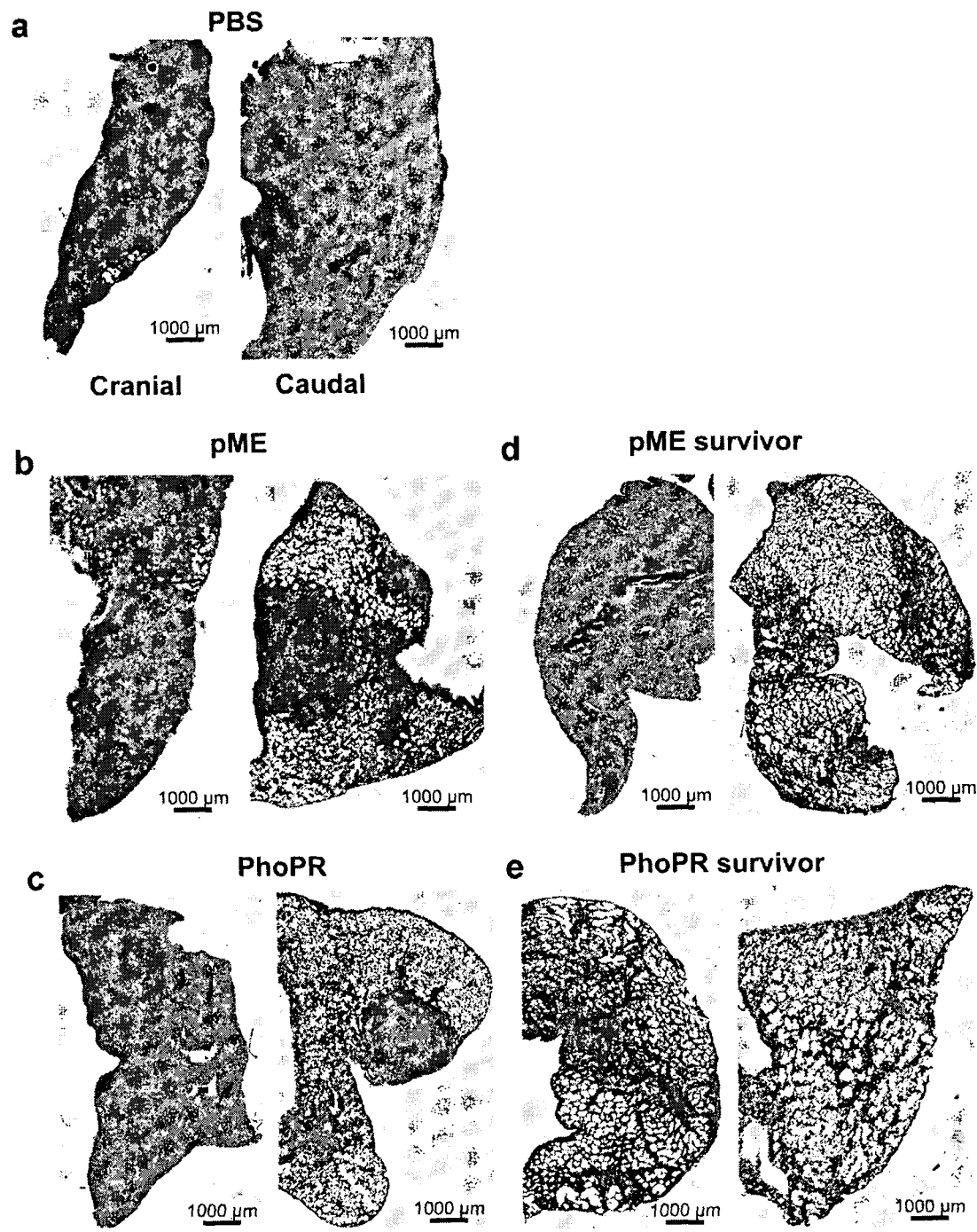

The lungs of five animals were subjected to histological analysis. They include one animal from each group that reached the humane endpoint, the sole survivor of the parental group, and one of the four survivors of the rBCG-Japan/PhoPR group at week 43. Interestingly, the mortality of guinea pigs appeared to be associated with the extent of tissue damage in the caudal lobe. The three animals euthanized before the end of experiment had extensive (FIG. 6a) or partial consolidation (FIG. 6b, c) in the caudal lobes in addition to extensive consolidation in the cranial lobes. In contrast, the two survivors appeared to have healthy tissues in the caudal lobe, despite the fact that the one from the parental group also had extensive tissue damage in the cranial lobe (FIG. 6d). Strikingly, the survivor of the rBCG-Japan/PhoPR group appeared to have normal lungs with no visible lung consolidation in either lobe (FIG. 6e).

PhoP is considered a virulence factor of M. tb[24] partially because it positively regulates the secretion of EsxA, an important effector of M. tb virulence[40]. As such, it is possible that overexpression of phoP-phoR in BCG may increase virulence and compromise safety. On the other hand, since esxA is part the region of difference 1 (RD1) that is absent in the genomes of all BCG strains[12], the extent to which overexpression of phoP-phoR contributes to BCG virulence remains unclear.

Figure 7:
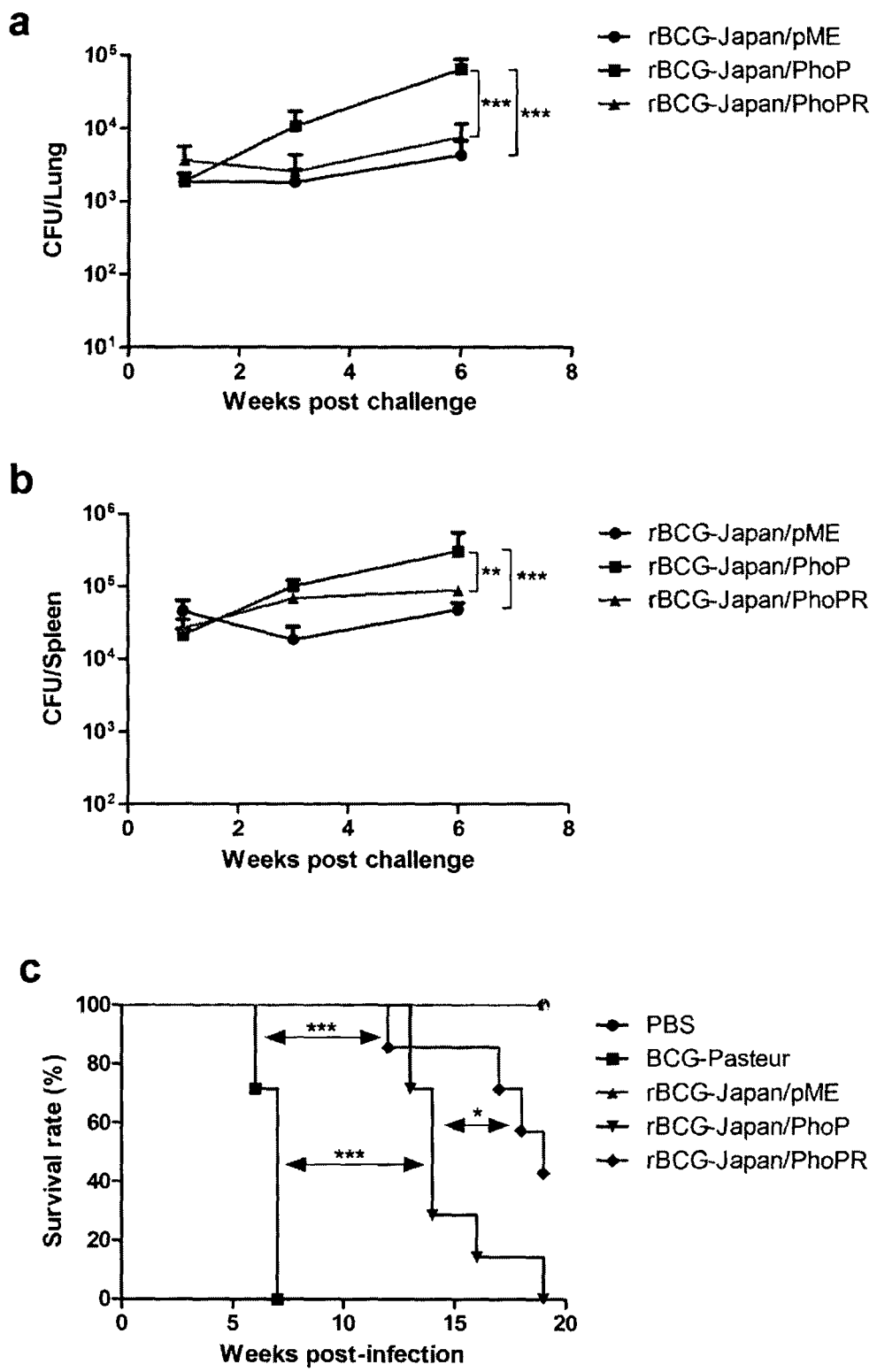

To address this, we first infected SCID mice with the recombinant BCG-Japan strains and monitored bacterial growth in target organs for up to 6 weeks. Interestingly, there was no significant difference between the growth of rBCG-Japan/PhoPR and the parental BCG in the lungs or spleen during the course of the experiment (FIG. 7a, b). However, overexpression of phoP alone increased replication of BCG-Japan in SCID mice compared to both the parental strain and rBCG-Japan/PhoPR.

Next, we performed a long-term SCID mice survival experiment. BCG-Pasteur, which is among the most virulent of the BCG strains[41], was also included in this experiment for comparison. The median survival time of SCID mice infected with BCG-Pasteur, rBCG-Japan/PhoP, and rBCG-Japan/PhoPR were 7, 14, and 19 weeks, respectively (FIG.

7c). All SCID mice infected with the parental strain or PBS survived until week 20 when the experiment was terminated. Log-rank analysis revealed that the rBCG-Japan/PhoP group had significantly reduced survival compared to the rBCG-Japan/PhoPR group (p=0.02) and the parental group (p<0.001), which is consistent with the higher bacterial burdens observed in this group in the short-term infection experiment (FIG. 7a, b). The rBCG-Japan/PhoPR group also showed reduced survival compared to the parental group (p=0.02). Importantly, both rBCG-Japan/PhoPR and rBCG-Japan/PhoP were significantly less virulent than BCG-Pasteur (p<0.001) in SCID mice. Taken together, these results suggest that the overexpression of phoP-phoR in BCG-Japan does not increase its replication in SCID mice and causes only a modest increase in virulence.

Taken together, we demonstrated that recombinant BCG overexpressing phoP-phoR confers enhanced protection against tuberculosis. The superior protection of rBCG-Japan/PhoPR was demonstrated in guinea pigs, evidenced by significantly prolonged survival and reduced pathology, which is a hallmark for testing novel vaccines in animal models. Guinea pigs are the "gold standard" animal model for testing TB vaccine efficacy'. The pathogenesis of disease, pathological lesions and response to BCG vaccination are similar to those described in humans.

There is consensus that novel TB vaccine candidates must meet criteria to advance from the discovery stage into pre-clinical development. These criteria include a robust induction of IFN-γ, better protective efficacy than BCG, and a comparable safety profile to BCG in the established animal models[42]. The rBCG-Japan/PhoPR strain has already satisfied these criteria and thus is a promising candidate for future clinical development.

M. bovis BCG is also used in the treatment of bladder cancer. Numerous randomized controlled clinical trials indicate that intravesical administration of BCG can prevent or delay tumor recurrence[43]. The details of how BCG exerts this effect remain to be determined. However, the antitumor response requires an intact T-cell response, and involves increased expression of Th1-type cytokines[44]. As such, a BCG strain such as rBCG-Japan/PhoPR demonstrating increased Th1 cytokine IFN-γ may provide enhanced antitumor activity.

In summary, we use recombinant BCG strains that overexpress phoP phoR as vaccines to prevent TB and other mycobacterial infections. These recombinant BCG vaccines induce better protective immunity against tuberculosis.

In the genetically engineered (i.e., recombinant) *Mycobacterium* of the invention, the PhoP and PhoR proteins are overexpressed, i.e., these two proteins are expressed at a level that exceeds that of a suitable control organism, such as the same *Mycobacterium* that has not been genetically engineered to overexpress PhoP and PhoR. Those of skill in the art are well acquainted with comparative measurements of protein activity, and with the use of suitable standards and controls for such measurements.

The overexpression of PhoP and PhoR proteins in a *Mycobacterium* may be carried out by any suitable method known in the art. Generally, the method will involve linking nucleic acid sequences encoding the PhoP and PhoR proteins to expression control sequences that are not, in nature, linked to phoP and phoR genes. Those of skill in the art will recognize that many such expression-control sequences are known and would be suitable for use in the invention. For example, if constitutive expression of phoP and phoR genes is desired, expression-control sequences (e.g., promoters and associated sequences) include but are not limited to: *Mycobacterium* optimal promoter: hsp65, ace or msp 12 promoter, T7 promoter, etc. Alternatively, overexpression of phoP and phoR may be inducible for example, under the tetracycline inducible promoters.

The proteins, polypeptides or peptides encoded according to the invention include naturally-occurring proteins, polypeptides or peptides, or the homologs thereof which have the same function as naturally-occurring proteins, polypeptides or peptides. Such homologs include proteins, polypeptides or peptides having at least 60%, preferably about 70% or more, 80% or more, and most preferably 90% or more, e.g., 95%, 96%, 97%, 98 or 99% homology to the amino acid sequences of the naturally-occurring proteins, polypeptides or peptides, e.g., to the amino acid sequences shown in SEQ ID NO: 1 and SEQ ID NO:3. Such homologs include proteins, polypeptides or peptides with substitution, addition and deletion of one or more (e.g., 1-50, 1-20, 1-10, 1-5) amino acid residues in the amino acid sequences of the naturally-occurring proteins, polypeptides or peptides (e.g., in the amino acid sequences shown in SEQ ID NO: 1 and SEQ ID NO:3). Such homologs include especially proteins, polypeptides or peptides with conserved amino acid substitution(s).

The term "PhoP" and "PhoR", as used therein, refer to the two-component regulatory system PhoP-PhoR. PhoP is a response regulator and PhoR is a histidine kinase. PhoP or PhoR encoded according to the invention includes naturally-occurring, functional PhoPs and PhoRs, e.g., from genus *Mycobacterium*, preferably from *Mycobacterium tuberculosis*, or *Mycobacterium bovis*, or the homologs thereof as described above. Exemplary amino acid sequences of PhoP and PhoR are presented in FIG. 1a SEQ ID NO:1 and FIG. 1c SEQ ID NO:3.

The term "overexpress", "overexpressing" or "overexpression", as used therein, refers to the protein level of a target gene expressed in a recombinant bacterium is higher than the level of the same protein expressed in the initial bacterium which is not recombinant. For example, the protein of interest expressed in a recombinant bacterium is 1.1, 1.5, 2, 4, 10, 20, 50, 100, 500, 1000 or more fold than a non-recombinant bacterium. The overexpression can be carried out by genetic engineering such as the use of a multiple copy plasmids and/or the use of strong promoters."

Variations of Nucleic Acid Molecules

Modifications

Many modifications may be made to the nucleic acid molecule DNA sequences disclosed in this application and these will be apparent to one skilled in the art. The invention includes nucleotide modifications of the sequences disclosed in this application (or fragments thereof) that encode proteins or peptides in bacterial or mammalian cells which have the same function as the proteins or peptides disclosed in this application. Modifications include substitution, insertion or deletion of one or more (e.g., 1-50, 1-20, 1-10, 1-5) nucleotides or altering the relative positions or order of one or more (e.g., 1-50, 1-20, 1-10, 1-5) nucleotides.

Nucleic acid molecules may encode conservative amino acid changes in PhoP and PhoR proteins. The invention includes functionally equivalent nucleic acid molecules that encode conservative amino acid changes and produce silent amino acid changes in PhoP and PhoR proteins. Methods for identifying empirically conserved amino acid substitution groups are well known in the art (see for example, Wu, Thomas D. "Discovering Empirically Conserved Amino Acid Substitution Groups in Databases of Protein Families" (http://www.ncbi.nlm.nih.gov:80/entrez/query.fcgi?cmd=Retrieve&db=PubMed&list_uids=8877523&dopt=Abstract).

Nucleic acid molecules may encode non-conservative amino acid substitutions, additions or deletions in phoP and/or phoR gene. The invention includes functionally equivalent nucleic acid molecules that make non-conservative amino acid changes within the amino acid sequences in PhoP and PhoR proteins. Functionally equivalent nucleic acid molecules include DNA and RNA that encode peptides, peptides and proteins having non-conservative amino acid substitutions (preferably substitution of a chemically similar amino acid), additions, or deletions but which also retain the same or similar function to the PhoP and PhoR proteins or peptides disclosed in this application. The invention includes the DNAs or RNAs encoding fragments or variants of PhoP and PhoR protein.

The fragments are useful as immunogens and in immunogenic compositions.

PhoP and PhoR like-activity of such fragments and variants is identified by assays as described below.

Sequence Identity

The nucleic acid molecules of the invention also include nucleic acid molecules (or a fragment thereof) having at least about: 60% identity, at least 70% identity, at least 80% identity, at least 90% identity, at least 95% identity, at least 96% identity, at least 97% identity, at least 98% identity or, most preferred, at least 99% or 99.5% identity to a nucleic acid molecule of the invention and which are capable of expression of nucleic acid molecules in bacterial or mammalian cells. Identity refers to the similarity of two nucleotide sequences that are aligned so that the highest order match is obtained. Identity is calculated according to methods known in the art. For example, if a nucleotide sequence (called “Sequence A”) has 90% identity to a portion of SEQ ID NO: 2, then Sequence A will be identical to the referenced portion of SEQ ID NO: 2 except that Sequence A may include up to 10 point mutations (such as substitutions with other nucleotides) per each 100 nucleotides of the referenced portion of SEQ ID NO: 2.

Sequence identity (each construct preferably without a coding nucleic acid molecule insert) is preferably set at least about: 70% identity, at least 80% identity, at least 90% identity, at least 95% identity, at least 96% identity, at least 97% identity, at least 98% identity or, most preferred, at least 99% or 99.5% identity to the sequences provided in SEQ ID NO: 2 or its complementary sequence). Sequence identity will preferably be calculated with the GCG program from Bioinformatics (University of Wisconsin). Other programs are also available to calculate sequence identity, such as the Clustal W program (preferably using default parameters; Thompson, J D et al., Nucleic Acid Res. 22:4673-4680), BLAST P, BLAST X algorithms, *Mycobacterium avium* BLASTN at The Institute for Genomic Research (http: tigrblast.tigr.org/), *Mycobacterium bovis, M. bovis* BCG (Pastuer), *M. marinum, M. leprae, M. tuberculosis* BLASTN at the Wellcome Trust Sanger Institute (http://www.sanger.ac.uk/Projects/Microbes/), *M. tuberculosis* BLAST searches at Institute Pasterur (Tuberculist) (http://genolist.pasteur.fr/TubercuList/), *M. leprae* BLAST searches at Institute Pasteur (Leproma) (http://genolist.pasteur.fr/Leproma/), *M. paratuberculosis* BLASTN at Microbial Genome Project, University of Minnesota (http://www.cbc.umn.edu/ResearchProjects/Ptb/ and http://www.cbc.umn.edu/ResearchProjects/AGAC/Mptb/Mptbhome.html), various BLAST searches at the National Center for Biotechnology Information—USA (http://www.ncbi.nlm.nih.gov/BLAST/) and various BLAST searches at GenomeNet (Bioinformatics Center—Institute for Chemical Research) (http://blast.genome.ad.jp/).

Since the genetic code is degenerate, the nucleic acid sequences in SEQ ID NO:2 and SEQ ID NO:4 are not the only sequences which may code for a polypeptide having PhoP and PhoR activities. This invention includes nucleic acid molecules that have the same essential genetic information as the nucleic acid molecules described in SEQ ID NO:2 and SEQ ID NO:4. Nucleic acid molecules (including RNA) having one or more nucleic acid changes compared to the sequences described in this application and which result in production of the polypeptides shown in SEQ ID NO:1 and SEQ ID NO:3 are within the scope of the invention.

Other functional equivalent forms of PhoP and PhoR proteins-encoding nucleic acids can be isolated using conventional DNA-DNA or DNA-RNA hybridization techniques.

Hybridization

The invention includes DNA that has a sequence with sufficient identity to a nucleic acid molecule described in this application to hybridize under stringent hybridization conditions (hybridization techniques are well known in the art). The present invention also includes nucleic acid molecules that hybridize to one or more of the sequences in [SEQ ID NO:2] and SEQ ID NO:4 or their complementary sequences. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.). High stringency washes have preferably low salt (preferably about 0.2% SSC) and a temperature of about 50-65° C.

Vaccines

One skilled in the art knows the preparation of live recombinant vaccines. Typically, such vaccines are prepared as injectable, either as liquid solutions or suspensions; solid forms suitable for solution in, or suspension in, liquid prior to injection may also be prepared. The preparation may also be emulsified, or the protein encapsulated in liposomes. The live immunogenic ingredients are often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants that enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn -glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80™ emulsion.

The effectiveness of an adjuvant may be determined by measuring the amount of antibodies directed against an immunogenic polypeptide containing a *Mycobacterium tuberculosis* antigenic sequence resulting from administration of the live recombinant *Mycobacterium bovis*-BCG vaccines that are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The vaccines are administered in a manner compatible with the dosage formulation, and in such amount as will be prophylactically and/or therapeutically effective.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the live recombinant *Mycobacterium bovis*-BCG vaccine administered in conjunction with other immuneregulatory agents, for example, immune globulins.

A subject of the present invention is also a multivalent vaccine formula comprising, as a mixture or to be mixed, a live recombinant *Mycobacterium bovis*-BCG vaccine as defined above with another vaccine, and in particular another recombinant live recombinant *Mycobacterium bovis*-BCG vaccine as defined above, these vaccines comprising different inserted sequences.

Pharmaceutical Compositions

The pharmaceutical compositions of this invention are used for the treatment or prophylaxis of a mammal against challenge by *Mycobacterium tuberculosis* or *Mycobacterium bovis*. The pharmaceutical compositions of this invention are also used to treat patients having degenerative diseases, disorders or abnormal physical states such as cancer.

The pharmaceutical compositions can be administered to humans or animals by methods such as tablets, aerosol administration, intratracheal instillation and intravenous injection.

EXAMPLES

Example 1: Cloning Vector pME

A kanamycin resistant shuttle vector which contains a T7 promoter was obtained as follows. The pDrive cloning vector (obtained from Qiagen) was cut with EcoRI and self-ligated to generate pDRI. The pDRI was digested with SspI and the 1903 bp fragment product was isolated. The pMD31 shuttle vector (Wu et al., 1993, *Molecular Microbiology,* 7, 407-417) was digested with SspI and the 3379 bp fragment was isolated. The two SspI generated fragments were ligated to generate pME (5282 bp), which contains the original T7 promoter of the pDRIVE. The cloning vector pME is shown in FIG. 2.

Example 2: Construction of Expression Vectors for phoP and phoP-phoR

An 1028 bp product containing phoP as well as the 257 bp upstream region of the phoP translational start site was amplified by PCR using a forward primer phoP-F (5'-AAAAAGGTACCGCTTGTTTGGCCATGTCAAC-3' (SEQ ID NO:5)) and a reverse primer phoP-R (5'-AAAAACTGCAGGCTGCCGATCCGATTAACTAC-3' (SEQ ID NO: 6)) which contain a KpnI and a PstI restriction site (underlined), respectively. Using these restriction sites, the PCR product was ligated to a shuttle vector pME (pME-PhoP). Similarly, a vector which expresses the phoP-phoR operon (pME-PhoPR) was constructed by cloning a 2501 bp PCR product—containing phoP and phoR (as well as the intergenic region between the two genes, 177 bp upstream of the phoP start codon, and 78 bp downstream of phoR stop codon)—into pME. This product was amplified by PCR from BCG-Pasteur genomic DNA using forward primer phoPR-F (5'-AAAAAGGTACCGGTCGCAATACCCACGAG-3' (SEQ ID NO: 7)) and reverse primer phoPR-R (5'-AAAAACTGCAGCCTCAGTGATTTCGGCTTTG-3' (SEQ ID NO: 8)) containing a KpnI and a PstI site (underlined), respectively. The constructs were confirmed by DNA sequencing.

The constructs as well as the empty vector pME were electroporated separately into BCG-Prague and BCG-Japan. Generation of a recombinant BCG was accomplished as follows: Cells of *M. bovis* BCG-Japan (ATCC 35737) and *M. bovis* BCG-Prague (ATCC 35742) were transformed with plasmid pME-PhoP or pME-PhoPR by electroporation, and electroporated cells were plated onto 7H11 media plates supplemented with 10% OADC (Difco) and 25 μg/ml of kanamycin. After 4 weeks of incubation at 37° C., individual colonies were selected and grown in 7H9 liquid media supplemented with 10% ADC (Difco) plus 25 μg/ml of kanamycin. After culturing for 3 weeks in this media, plasmid DNA from the selected clones was isolated and confirmed by DNA sequencing. Frozen stocks of recombinant BCG strains were subsequently made by mixing 1 ml of culture with 1 ml of 50% sterile glycerol solution and stored at −80° C.

The constructed expression vectors for phoP and phoP-phoR are shown in FIG. 3.

Example 3: rBCG-Japan/PhoPR Induces More IFN-γ Production by $CD4^+$ T Cells than Parental BCG Female C57BL/6 mice were purchased from Charles River Laboratories and were age-matched (6 weeks) within each experiment. Four mice per group were inoculated subcutaneously on the scruff of the neck with approximately $5\times10^4$ CFU in 0.2 ml PBS/0.01% Tween 80 of BCG strains. Control mice were given 0.2 mL of PBS/0.01% Tween 80. After 8 weeks, mice were euthanized, splenocytes were isolated. Quantitative measurements of IFN-γ production was determined using an enzyme-linked immunosorbant assay (ELISA) using the OptEIA Mouse IFN-γ ELISA set (BD Biosciences). Samples used for ELISAs were supernatants from splenocytes stimulated by PPD (10 µg/ml) for 72 hours. Briefly, samples were added in triplicate to 96-well, flat-bottomed plates (Nunc MaxiSorp) pre-coated with capture antibody and measurements were carried out following the manufacturer's protocol. The absorbance was read at 450 nm on a microplate reader (TECAN infinite M200). IFN-γ levels were calculated based on a standard curve generated using an IFN-γ standard. The results are shown in FIGS. 4a and 4b. Data are shown as mean±SEM, after subtraction of reading from samples without PPD stimulation. In FIG. 4a, the two-tailed unpaired student t-test was performed; in FIG. 4b, One-way ANOVA and Bonferroni multiple comparison tests were performed. *p<0.05, p<0.01, *p<0.001.

To determine the source of IFN-γ induced by the recombinant BCG strains, we also performed intracellular cytokine staining and FACS analyses. Briefly, splenocytes were seeded at $2 \times 10^6$ cells/well in 100 µl in triplicate and stimulated with 2.5 µg/well of purified protein derivative (PPD) (Statens Serum Institute, Denmark) or complete RPMI (cRPMI; RPMI/10% FBS/1% L-glutamine/1% penicillin/streptomycin) as a control and incubated at 37° C. and 5% $CO_2$. After 19 hours of stimulation, GolgiPlug (BD Biosciences) was added in a 1:1000 final dilution and incubated for an additional 5 hours. After a total of 24 hours stimulation, plates were centrifuged at 1400 rpm for 5 minutes at 4° C. The supernatant was removed and the cell pellet was washed in 200 µl FACS Buffer (0.5% BSA/PBS), and resuspended in Fc Block (eBiosciences) diluted in FACS Buffer (1:400) and incubated for 15 minutes on ice in the dark. An additional 150 µl of FACS Buffer was added, mixed, and plates were centrifuged at 1400 rpm for 5 minutes at 4° C. Supernatant was removed and cells were stained for extracellular T cell surface markers: CD3-PE, CD4-FITC, and CD8a-PercyPCy5.5 (BD Biosciences) diluted in FACS Buffer, and incubated for 30 minutes on ice in the dark. Following extracellular marker staining, the cells were washed with 150 µl FACS Buffer and permeabilized and fixed with 1× CytoFix/CytoPerm (BD Biosciences) for 20 minutes. Cells were then washed with 1× PermWash (BD Biosciences) and incubated with IFN-γ-APC (BD Biosciences) for 30 minutes to stain for intracellular IFN-γ. Cells were centrifuged as above, resuspended in 200 µl FACS Buffer, and analyzed on a BD FACSCalibur™ flow cytometer (BD Biosciences). A total of 300 000 events per sample were collected in the lymphocyte gate and analyzed using FlowJo V7.6. Gates for analysis were set based on isotype controls. Data are shown as mean±SEM, after subtraction of reading from samples without PPD stimulation. The result is shown in FIG. 4c, and one-way ANOVA and Bonferroni multiple comparison tests were performed for statistical analysis. *p<0.05, p<0.01, *p<0.001.

Example 4: rBCG-Japan/PhoPR Prolongs the Survival of Guinea Pies Infected with *M. tb*

Groups of 11 female Hartely guinea pigs (200-250 g) were purchased from Charles River Laboratories, and they were vaccinated subcutaneously with $5 \times 10^4$ CFU of BCG-Japan containing pME (rBCG-Japan/pME), pME-PhoPR (rBCG-Japan/PhoPR) in 0.2 ml PBS/0.01% Tween80 or PBS/0.01% Tween80 alone as a control. At eight weeks post-vaccination, guinea pigs were challenged with 1,000 CFU of *M. tb* H37Rv by an aerosol route using a GlasCol nebulizer. Guinea pigs were euthanized at the humane end-point and survival curves were plotted using the Kaplan-Meier method. The result is shown in FIG. 5*a*. Log-rank test was performed to compare each pair of the survival curves. *$p<0.05$, $p<0.01$, *$p<0.0001$.

The lungs and spleen of guinea pigs euthanized at the humane end-point were harvested. The spleen and the entire right lung were homogenized separately and plated on 7H11 agar to quantify the *M. tb* burden in each organ. Colonies were counted after incubation at 37° C. for three weeks. The results are shown in FIGS. 5*b* and 5*c*. The organ weights of all animals in each group were measured and the results are shown in FIGS. 5*d* and 5*e*. Data in FIGS. 5*b* to 5*e* are shown as mean±SEM, and One-way ANOVA and Bonferroni multiple comparison tests were performed. *$p<0.05$, $p<0.01$, *$p<0.001$.

Example 5: rBCG-Japan/PhoPR Reduces the Lung Pathology of Guinea Pies Infected with *M. tb*

Six guinea pigs from the experiment described in FIG. 4 were chosen for histology analysis. These include one guinea pig from each group that reached the humane end-point at weeks 25, 27, and 39, respectively (FIGS. 6*a* to 6*c*). The pME (FIG. 6*b*) and PhoPR (FIG. 6*c*) guinea pigs represent the sixth animal to be euthanized from each group (median). The sole survivor of the pME group (FIG. 6*d*) and one randomly chosen survivor of the PhoPR group (FIG. 6*e*) were included. For each guinea pig, sections of caudal and cranial lobes of the left lungs were analyzed by hematoxylin-eosin staining. Briefly, formalin-fixed tissues were embedded into paraffin blocks. Serial sections (5 μm thick) were prepared and they went through deparafinization process with three changes of xylene (3 minutes each) before being rehydrated with four washes of alcohol (100%, 100%, 95%, 70%, 3 minutes each). Sections were stained with hematoxylin and eosin (EMD Chemicals) and examined using Cytation™ 5 (BioTek).

Example 6: rBCG-Japan/PhoPR is Safe in SCID Mice

Short-term bacterial burden assay: Female Fox Chase CB17 SCID mice (Charles River Laboratories) were age-matched (7 weeks old). Groups of 12 mice were infected intravenously via a lateral tail vein with $10^5$ CFU of rBCG-Japan/pME, rBCG-Japan/ PhoP, or rBCG-Japan/PhoPR in 0.2 mL of PBS/0.01% Tween80 or PBS/0.01% Tween80 alone as a control. At weeks 1, 3, and 6 post-infection, mice (n=4 at each time point) were euthanized and the lungs and spleen were harvested, homogenized in PBS, and plated on 7H11 agar to determine bacterial burden in the lungs (FIG. 7*a*) and spleen (FIG. 7*b*). Data are showed as mean±SD. Two-Way ANOVA and Bonferroni multiple comparison tests were performed. *$p<0.05$, $p<0.01$, *$p<0.001$.

Long term survival assay: Groups of ten age-matched female SCID mice (7 weeks old) from Charles River Laboratories were infected intravenously via a lateral tail vein with $10^7$ CFU of BCG-Pasteur, three aforementioned recombinant BCG-Japan strains or PBS/0.01% Tween80 as described above. Three mice from each group were euthanized at day 1 post-infection (for assessing infection dose) while the remaining mice were monitored weekly until they reached a humane endpoint (loss of 20% maximal body weight). Survival curves were plotted using the Kaplan-Meier method. The results are shown in FIG. 7*c*. Log-rank test was performed to compare each pair of the survival curves. *$p<0.05$, ***$p<0.001$.

REFERENCES

1. Colditz, G. A., et al. The efficacy of bacillus Calmette-Guerin vaccination of newborns and infants in the prevention of tuberculosis: meta-analyses of the published literature. *Pediatrics* 96, 29-35 (1995).
2. Trunz, B. B., Fine, P. & Dye, C. Effect of BCG vaccination on childhood tuberculous meningitis and miliary tuberculosis worldwide: a meta-analysis and assessment of cost-effectiveness. *Lancet* 367, 1173-1180 (2006).
3. Brewer, T. F. Preventing tuberculosis with bacillus Calmette-Guerin vaccine: a meta-analysis of the literature. *Clin Infect Dis* 31 Suppl 3, S64-67 (2000).
4. Colditz, G. A., et al. Efficacy of BCG vaccine in the prevention of tuberculosis. Meta-analysis of the published literature. *JAMA* 271, 698-702 (1994).
5. Fine, P. E. Variation in protection by BCG: implications of and for heterologous immunity. *Lancet* 346, 1339-1345 (1995).
6. Behr, M. A. BCG-different strains, different vaccines? *Lancet Infect Dis* 2, 86-92 (2002).
7. Behr, M. A. & Small, P. M. A historical and molecular phylogeny of BCG strains. *Vaccine* 17, 915-922 (1999).
8. Brosch, R., et al. Genome plasticity of BCG and impact on vaccine efficacy. *Proc Natl Acad Sci USA* 104, 5596-5601 (2007).
9. Leung, A. S., et al. Novel genome polymorphisms in BCG vaccine strains and impact on efficacy. *BMC Genomics* 9, 413 (2008).
10. Garcia Pelayo, M. C., et al. A comprehensive survey of single nucleotide polymorphisms (SNPs) across *Mycobacterium bovis* strains and *M. bovis* BCG vaccine strains refines the genealogy and defines a minimal set of SNPs that separate virulent *M. bovis* strains and *M. bovis* BCG strains. *Infect Immun* 77, 2230-2238 (2009).
11. Mahairas, G. G., Sabo, P. J., Hickey, M. J., Singh, D. C. & Stover, C. K. Molecular analysis of genetic differences between *Mycobacterium bovis* BCG and virulent *M. bovis*. *J Bacteriol* 178, 1274-1282 (1996).
12. Behr, M. A., et al. Comparative genomics of BCG vaccines by whole-genome DNA microarray. *Science* 284, 1520-1523 (1999).
13. Horwitz, M. A., Harth, G., Dillon, B. J. & Maslesa-Galic, S. Commonly administered BCG strains including an evolutionarily early strain and evolutionarily late strains of disparate genealogy induce comparable protective immunity against tuberculosis. *Vaccine* 27, 441-445 (2009).
14. Ritz, N., Hanekom, W. A., Robins-Browne, R., Britton, W. J. & Curtis, N. Influence of BCG vaccine strain on the immune response and protection against tuberculosis. *FEMS Microbiol Rev* 32, 821-841 (2008).
15. Skeiky, Y. A. & Sadoff, J. C. Advances in tuberculosis vaccine strategies. *Nat Rev Microbiol* 4, 469-476 (2006).
16. Andersen, P. & Kaufmann, S. H. Novel vaccination strategies against tuberculosis. *Cold Spring Harb Perspect Med* 4(2014).
17. Tameris, M. D., et al. Safety and efficacy of MVA85A, a new tuberculosis vaccine, in infants previously vaccinated with BCG: a randomised, placebo-controlled phase 2b trial. *Lancet* (2013).
18. Developing whole mycobacteria cell vaccines for tuberculosis: Workshop proceedings, Max Planck Institute for Infection Biology, Berlin, Germany, Jul. 9, 2014. *Vaccine* 33, 3047-3055 (2015).
19. Horwitz, M. A., Harth, G., Dillon, B. J. & Maslesa-Galic, S. Recombinant bacillus calmette-guerin (BCG) vaccines expressing the *Mycobacterium tuberculosis* 30-kDa major secretory protein induce greater protective immunity against tuberculosis than conventional BCG vaccines in a highly susceptible animal model. *Proc Natl Acad Sci USA* 97, 13853-13858 (2000).
20. Horwitz, M. A. & Harth, G. A new vaccine against tuberculosis affords greater survival after challenge than the current vaccine in the guinea pig model of pulmonary tuberculosis. *Infect Immun* 71, 1672-1679 (2003).
21. Grode, L., et al. Increased vaccine efficacy against tuberculosis of recombinant *Mycobacterium bovis* bacille Calmette-Guerin mutants that secrete listeriolysin. *J Clin Invest* 115, 2472-2479 (2005).
22. Desel, C., et al. Recombinant BCG DeltaureC hly+ induces superior protection over parental BCG by stimulating a balanced combination of type 1 and type 17 cytokine responses. *J Infect Dis* 204, 1573-1584 (2011).
23. Williams, A., et al. Evaluation of vaccines in the EU TB Vaccine Cluster using a guinea pig aerosol infection model of tuberculosis. *Tuberculosis (Edinb)* 85, 29-38 (2005).
24. Martin, C., et al. The live *Mycobacterium tuberculosis* phoP mutant strain is more attenuated than BCG and confers protective immunity against tuberculosis in mice and guinea pigs. *Vaccine* 24, 3408-3419 (2006).
25. Aguilar, D., et al. Immunological responses and protective immunity against tuberculosis conferred by vaccination of Balb/C mice with the attenuated *Mycobacterium tuberculosis* (phoP) SO2 strain. *Clin Exp Immunol* 147, 330-338 (2007).
26. Arbues, A., et al. Construction, characterization and preclinical evaluation of MTBVAC, the first live-attenuated *M. tuberculosis*-based vaccine to enter clinical trials. *Vaccine* 31, 4867-4873 (2013).
27. Ritz, N., et al. The influence of bacille Calmette-Guerin vaccine strain on the immune response against tuberculosis: a randomized trial. *Am J Respir Crit Care Med* 185, 213-222 (2012).
28. Vallishayee, R. S., Shashidhara, A. N., Bunch-Christensen, K. & Guld, J. Tuberculin sensitivity and skin lesions in children after vaccination with 11 different BCG strains. *Bull World Health Organ* 51, 489-494 (1974).
29. Ladefoged, A., Bunch-Christensen, K. & Guld, J. Tuberculin sensitivity in guinea-pigs after vaccination with varying doses of BCG of 12 different strains. *Bull World Health Organ* 53, 435-443 (1976).
30. Milstien, J. B. & Gibson, J. J. Quality control of BCG vaccine by WHO: a review of factors that may influence vaccine effectiveness and safety. *Bull World Health Organ* 68, 93-108 (1990).
31. Walters, S. B., et al. The *Mycobacterium tuberculosis* PhoPR two-component system regulates genes essential for virulence and complex lipid biosynthesis. *Mol Microbiol* 60, 312-330 (2006).
32. Cooper, A. M. Cell-mediated immune responses in tuberculosis. *Annu Rev Immunol* 27, 393-422 (2009).
33. North, R. J. & Jung, Y. J. Immunity to tuberculosis. *Annu Rev Immunol* 22, 599-623 (2004).
34. Black, G. F., et al. BCG-induced increase in interferon-gamma response to mycobacterial antigens and efficacy of BCG vaccination in Malawi and the UK: two randomised controlled studies. *Lancet* 359, 1393-1401 (2002).
35. Comstock, G. W. Identification of an effective vaccine against tuberculosis. *Am Rev Respir Dis* 138, 479-480 (1988).
36. Fine, P. E., Sterne, J. A., Ponnighaus, J. M. & Rees, R. J. Delayed-type hypersensitivity, mycobacterial vaccines and protective immunity. *Lancet* 344, 1245-1249 (1994).

37. Castillo-Rodal, A. I., et al. *Mycobacterium bovis* BCG substrains confer different levels of protection against *Mycobacterium tuberculosis* infection in a BALB/c model of progressive pulmonary tuberculosis. *Infect Immun* 74, 1718-1724 (2006).
38. Lalor, M. K., et al. Population differences in immune responses to Bacille Calmette-Guerin vaccination in infancy. *J Infect Dis* 199, 795-800 (2009).
39. Gallant, C. J., et al. Tuberculin skin test and in vitro assays provide complementary measures of antimycobacterial immunity in children and adolescents. *Chest* 137, 1071-1077 (2010).
40. Frigui, W., et al. Control of *M. tuberculosis* ESAT-6 secretion and specific T cell recognition by PhoP. *PLoS Pathog* 4, e33 (2008).
41. Zhang, L., et al. Variable Virulence and Efficacy of BCG Vaccine Strains in Mice and Correlation With Genome Polymorphisms. *Mol Ther* 24, 398-405 (2016).

42. Barker, L., Hessel, L. & Walker, B. Rational approach to selection and clinical development of TB vaccine candidates. *Tuberculosis* (*Edinb*) 92 Suppl 1, S25-29 (2012).

43. Lamm, D. L. Efficacy and safety of bacille Calmette-Guerin immunotherapy in superficial bladder cancer. *Clin Infect Dis* 31 Suppl 3, S86-90 (2000).
44. Prescott, S., Jackson, A. M., Hawkyard, S. J., Alexandroff, A. B. & James, K. Mechanisms of action of intravesical bacille Calmette-Guerin: local immune mechanisms. *Clin Infect Dis* 31 Suppl 3, S91-93 (2000).

The invention claimed is:

1. A live recombinant *Mycobacterium bovis*-BCG strain comprising nucleic acids capable of overexpression and overexpressing both PhoP and PhoR proteins, the recombinant *Mycobacterium bovis*-BCG strain having improved immunogenicity compared to wild type nonrecombinant *Mycobacterium bovis*-BCG strain, the recombinant *Mycobacterium bovis*-BCG strain having virulence comparable with wild type nonrecombinant *Mycobacterium bovis*-BCG strain, and the recombinant *Mycobacterium bovis*-BCG strain having a decreased virulence compared to recombinant *Mycobacterium bovis*-BCG strain overexpressing only PhoP.

2. The live recombinant *Mycobacterium bovis*-BCG strain of claim 1, wherein the PhoP and PhoR proteins are from *Mycobacterium tuberculosis* or *Mycobacterium bovis*.

3. The live recombinant *Mycobacterium bovis*-BCG strain of claim 1, wherein the nucleic acids encode
(i) the amino acid sequence shown in SEQ ID NO: 1; or
(ii) a PhoP protein with the substitution, addition, or deletion of one or more amino acids in the amino acid sequence shown in SEQ ID NO: 1; or p1 (iii) the amino acid sequence shown in SEQ ID NO: 3; or
(iv) a PhoR protein with the substitution, addition, or deletion of one or more amino acids in the amino acid sequence shown in SEQ ID NO: 3.

4. The live recombinant *Mycobacterium bovis*-BCG strain of claim 1, wherein the nucleic acids comprise
(i) the nucleotide sequence shown in SEQ ID NO: 2; or
(ii) a sequence that hybridizes to the nucleotide sequence of (i) under a stringent hybridization condition; or
(iii) a sequence having at least 60% sequence identity to the nucleotide sequence shown in SEQ ID NO: 2; or
(iv) the nucleotide sequence shown in SEQ ID NO: 4; or
(v) a sequence that hybridizes to the nucleotide sequence of (iv) under a stringent hybridization condition; or
(vi) a sequence having at least 60% sequence identity to the nucleotide sequence shown in SEQ ID NO: 4.

5. The live recombinant *Mycobacterium bovis*-BCG strain of claim 1 wherein the nucleic acid molecule has undergone modification.

6. The live recombinant *Mycobacterium bovis*-BCG strain of claim 1 wherein the *Mycobacterium bovis*-BCG strain is selected from *Mycobacterium bovis*-BCG-Russia (ATCC number: 35740), *Mycobacterium bovis*-BCG-Moreau (ATCC number: 35736), *Mycobacterium bovis*-BCG-Japan (ATCC number: 35737), *Mycobacterium bovis*-BCG-Sweden (ATCC number: 35732), *Mycobacterium bovis*-BCG-Birkhaug (ATCC number: 35731), *Mycobacterium bovis*-BCG-Prague (ATCC number: 35742), *Mycobacterium bovis*-BCG-Glaxo (ATCC number: 35741), *Mycobacterium bovis*-BCG-Denmark (ATCC number: 35733), *Mycobacterium bovis*-BCG-Tice (ATCC numbers: 35743, 27289), *Mycobacterium bovis*-BCG-Frappier (ATCC: 35746, SM-R; ATCC: 35747, INH-R), *Mycobacterium bovis*-BCG-Connaught (ATCC: 35745), *Mycobacterium bovis*-BCG-Phipps (ATCC number: 35744), *Mycobacterium bovis*-BCG-Pasteur (ATCC number: 35734), BCG-Mexican (ATCC number: 35738) and *Mycobacterium bovis*-BCG-China (Shanghai Institute of Biological Product).

7. A pharmaceutical composition comprising the live recombinant *Mycobacterium bovis*-BCG strain of claim 1.

8. The recombinant *Mycobacterium bovis*-BCG strain of claim 1, wherein the PhoR of the recombinant *Mycobacterium bovis*-BCG strain is overexpressed by at least 10 fold as compared to an amount of PhoR expressed in the wild type nonrecombinant *Mycobacterium bovis*-BCG strain.

9. The recombinant *Mycobacterium bovis*-BCG strain of claim 1, wherein the PhoP of the recombinant *Mycobacterium bovis*-BCG strain is overexpressed by at least 10 fold as compared to an amount of PhoP expressed in the wild type nonrecombinant *Mycobacterium bovis*-BCG strain.

* * * * *

SEQUENCE LISTING

```
<160> NUMBER OF SEQ ID NOS: 8

<210> SEQ ID NO 1
<211> LENGTH: 247
<212> TYPE: PRT
<213> ORGANISM: Mycobacterium bovis

<400> SEQUENCE: 1

Met Arg Lys Gly Val Asp Leu Val Thr Ala Gly Thr Pro Gly Glu Asn
1               5                   10                  15

Thr Thr Pro Glu Ala Arg Val Leu Val Val Asp Asp Glu Ala Asn Ile
            20                  25                  30

Val Glu Leu Leu Ser Val Ser Leu Lys Phe Gln Gly Phe Glu Val Tyr
        35                  40                  45

Thr Ala Thr Asn Gly Ala Gln Ala Leu Asp Arg Ala Arg Glu Thr Arg
    50                  55                  60

Pro Asp Ala Val Ile Leu Asp Val Met Met Pro Gly Met Asp Gly Phe
65                  70                  75                  80

Gly Val Leu Arg Arg Leu Arg Ala Asp Gly Ile Asp Ala Pro Ala Leu
                85                  90                  95

Phe Leu Thr Ala Arg Asp Ser Leu Gln Asp Lys Ile Ala Gly Leu Thr
            100                 105                 110

Leu Gly Gly Asp Asp Tyr Val Thr Lys Pro Phe Ser Leu Glu Glu Val
        115                 120                 125

Val Ala Arg Leu Arg Val Ile Leu Arg Arg Ala Gly Lys Gly Asn Lys
    130                 135                 140

Glu Pro Arg Asn Val Arg Leu Thr Phe Ala Asp Ile Glu Leu Asp Glu
145                 150                 155                 160

Glu Thr His Glu Val Trp Lys Ala Gly Gln Pro Val Ser Leu Ser Pro
                165                 170                 175

Thr Glu Phe Thr Leu Leu Arg Tyr Phe Val Ile Asn Ala Gly Thr Val
            180                 185                 190

Leu Ser Lys Pro Lys Ile Leu Asp His Val Trp Arg Tyr Asp Phe Gly
        195                 200                 205

Gly Asp Val Asn Val Val Glu Ser Tyr Val Ser Tyr Leu Arg Arg Lys
    210                 215                 220

Ile Asp Thr Gly Glu Lys Arg Leu Leu His Thr Leu Arg Gly Val Gly
225                 230                 235                 240

Tyr Val Leu Arg Glu Pro Arg
                245
```

<210> SEQ ID NO 2
<211> LENGTH: 744
<212> TYPE: DNA
<213> ORGANISM: Mycobacterium bovis

<400> SEQUENCE: 2
atgcggaaag ggttgatct cgtgacggcg ggaaccccag gcgaaaacac cacaccggag 60
gctcgtgtcc tcgtggtcga tgatgaggcc aacatcgttg aactgctgtc ggtgagcctc 120
aagttccagg gctttgaagt ctacaccgcg accaacgggg cacaggcgct ggatcgggcc 180
cgggaaaccc ggccggacgc ggtgatcctc gatgtgatga tgcccgggat ggacggcttt 240
ggggtgctgc gccggctgcg cgccgacggc atcgatgccc cggcgttgtt cctgacggcc 300
cgtgactcgc tacaggacaa gatcgcgggt ctgaccctgg gtggtgacga ctatgtgaca 360
aagcccttca gtttggagga ggtcgtggcc aggctgcggg tcatcctgcg acgcgcgggc 420
aagggcaaca aggaaccacg taatgttcga ctgacgttcg ccgatatcga gctcgacgag 480
gagacccacg aagtgtggaa ggcgggccaa ccggtgtcgc tgtcgcccac cgaattcacc 540
ctgctgcgct atttcgtgat caacgcgggc accgtgctga gcaagcctaa gattctcgac 600
cacgtttggc gctacgactt cggtggtgat gtcaacgtcg tcgagtccta cgtgtcgtat 660
ctgcgccgca agatcgacac tggggagaag cggctgctgc acacgctgcg cggggtgggc 720
tacgtactgc gggagcctcg atga 744

<210> SEQ ID NO 3
<211> LENGTH: 485
<212> TYPE: PRT
<213> ORGANISM: Mycobacterium bovis

<400> SEQUENCE: 3

Met Ala Arg His Leu Arg Gly Arg Leu Pro Leu Arg Val Arg Leu Val
1 5 10 15

Ala Ala Thr Leu Ile Leu Val Ala Thr Gly Leu Val Ala Ser Gly Ile
20 25 30

Ala Val Thr Ser Met Leu Gln His Arg Leu Thr Ser Arg Ile Asp Arg
35 40 45

Val Leu Leu Glu Glu Ala Gln Ile Trp Ala Gln Ile Thr Leu Pro Leu
50 55 60

Ala Pro Asp Pro Tyr Pro Ile His Asn Pro Asp Arg Pro Pro Ser Arg
65 70 75 80

Phe Tyr Val Arg Val Ile Ser Pro Asp Gly Gln Ser Tyr Thr Ala Leu
85 90 95

Asn Asp Asn Thr Ala Ile Pro Ala Val Pro Ala Asn Asn Asp Val Gly
100 105 110

Arg His Pro Thr Thr Leu Pro Ser Ile Gly Gly Ser Lys Thr Leu Trp
115 120 125

Arg Ala Val Ser Val Arg Ala Ser Asp Gly Tyr Leu Thr Thr Val Ala
130 135 140

Ile Asp Leu Ala Asp Val Arg Ser Thr Val Arg Ser Leu Val Leu Leu
145 150 155 160

Gln Val Gly Ile Gly Ser Ala Val Leu Val Val Leu Gly Val Ala Gly
165 170 175

Tyr Ala Val Val Arg Arg Ser Leu Arg Pro Leu Ala Glu Phe Glu Gln
180 185 190

Thr Ala Ala Ala Ile Gly Ala Gly Gln Leu Asp Arg Arg Val Pro Gln
195 200 205

```
Trp His Pro Arg Thr Glu Val Gly Arg Leu Ser Leu Ala Leu Asn Gly
    210                 215                 220
Met Leu Ala Gln Ile Gln Arg Ala Val Ala Ser Ala Glu Ser Ser Ala
225                 230                 235                 240
Glu Lys Ala Arg Asp Ser Glu Asp Arg Met Arg Gln Phe Ile Thr Asp
                245                 250                 255
Ala Ser His Glu Leu Arg Thr Pro Leu Thr Thr Ile Arg Gly Phe Ala
            260                 265                 270
Glu Leu Tyr Arg Gln Gly Ala Ala Arg Asp Val Gly Met Leu Leu Ser
        275                 280                 285
Arg Ile Glu Ser Glu Ala Ser Arg Met Gly Leu Leu Val Asp Asp Leu
    290                 295                 300
Leu Leu Leu Ala Arg Leu Asp Ala His Arg Pro Leu Glu Leu Cys Arg
305                 310                 315                 320
Val Asp Leu Leu Ala Leu Ala Ser Asp Ala Ala His Asp Ala Arg Ala
                325                 330                 335
Met Asp Pro Lys Arg Arg Ile Thr Leu Glu Val Leu Asp Gly Pro Gly
            340                 345                 350

Thr Pro Glu Val Leu Gly Asp Glu Ser Arg Leu Arg Gln Val Leu Arg
        355                 360                 365
Asn Leu Val Ala Asn Ala Ile Gln His Thr Pro Glu Ser Ala Asp Val
    370                 375                 380
Thr Val Arg Val Gly Thr Glu Gly Asp Asp Ala Ile Leu Glu Val Ala
385                 390                 395                 400
Asp Asp Gly Pro Gly Met Ser Gln Glu Asp Ala Leu Arg Val Phe Glu
                405                 410                 415
Arg Phe Tyr Arg Ala Asp Ser Ser Arg Ala Arg Ala Ser Gly Gly Thr
            420                 425                 430

Gly Leu Gly Leu Ser Ile Val Asp Ser Leu Val Ala Ala His Gly Gly
        435                 440                 445
Ala Val Thr Val Thr Thr Ala Leu Gly Glu Gly Cys Cys Phe Arg Val
    450                 455                 460
Ser Leu Pro Arg Val Ser Asp Val Asp Gln Leu Ser Leu Thr Pro Val
465                 470                 475                 480
Val Pro Gly Pro Pro
                485
```

<210> SEQ ID NO 4
<211> LENGTH: 1458
<212> TYPE: DNA
<213> ORGANISM: Mycobacterium bovis

<400> SEQUENCE: 4

```
atggccagac accttcgagg aaggctgccc ctacgggtac gcctggtcgc agccacgctg      60
atcctggtgg ccactggact tgtggcctcg gggatcgcgg tcacctcgat gttgcagcac     120
cggctgacca gccggatcga tcgggtgttg ctcgaggaag cccaaatctg ggcgcagatc     180
acgctgccct tggcgccgga cccctaccct attcataacc ccgatcggcc gccgtcgagg     240
ttctacgttc gggtgatcag ccccgacggc cagagctata cggcactcaa cgacaacact     300
gccataccgg cggtgcccgc caacaatgat gtcggccggc acccgacgac gctgccatcg     360
atcggcggat ccaagacttt atggcgcgcg gtctcggtgc gcgcgtcgga tggctacttg     420
accaccgtcg ccattgatct ggccgacgtc cggagcaccg tgcggtcact ggtgctgttg     480
```

-continued

```
caggtcggca taggcagtgc ggtgctggtt gtcctcgggg tggcgggcta cgctgtggtt    540
cgccgcagcc tgcggccgct ggcagaattc gagcagacgg ccgcggcgat cggcgcgggg    600
cagctggatc gccgggtccc gcagtggcat ccgcgaactg aggtcggccg gctttcgttg    660
gcgctcaacg gaatgctggc acaaattcag cgggcggtgg cgtccgcgga atcttccgcc    720
gaaaaggccc gggattcaga ggaccggatg cgacagttca tcaccgacgc cagccatgaa    780
ctgcgtaccc cgttgaccac tatccgcggc ttcgcggagc tgtaccgaca aggagccgcc    840
cgcgacgtgg gcatgctgct gtcgcggatt gagagcgaag cgagccggat ggggctgctg    900
gtggacgatt tgctgctgct tgcccggcta gatgcgcacc ggccgttgga actgtgccgg    960
gtggacctgc tggcgctggc cagtgatgcc gcgcacgacg cgcgggcgat ggaccccaaa   1020
cgcaggatca ccctggaggt ccttgacggc cccggcaccc cggaggtcct cggcgacgaa   1080
tcgcggcttc ggcaggtgct gcgcaatctc gttgcaaatg ccatacagca caccccggaa   1140
agcgccgacg tcaccgtgcg agtcggcacc gagggcgacg acgccatcct cgaggtcgcc   1200
gatgacggtc cgggcatgag tcaggaggat gcgctgcggg tgttcgagcg gttctatcgc   1260
gccgactcgt cgcgggcgcg cgccagcggc gggaccggac tggggttgtc gatcgtcgac   1320
tctttggtgg cggcccatgg cggagcggtc accgtgacga ccgcgctcgg ggagggttgc   1380
tgctttcgtg tctcgctgcc gcgcgtcagt gacgtggacc agctgagcct cacgccagtt   1440
gtgccagggc gcccctga                                                 1458
```

```
<210> SEQ ID NO 5
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 5
aaaaaggtac cgcttgtttg gccatgtcaa c                                    31

<210> SEQ ID NO 6
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 6
aaaaactgca ggctgccgat ccgattaact ac                                   32

<210> SEQ ID NO 7
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 7
aaaaaggtac cggtcgcaat acccacgag                                       29

<210> SEQ ID NO 8
<211> LENGTH: 31
<212> TYPE: DNA
<213> ORGANISM: Artificial Sequence
<220> FEATURE:
<223> OTHER INFORMATION: Synthetic Polynucleotide
```

```
<400> SEQUENCE: 8
aaaaactgca gcctcagtga tttcggcttt g                              31
```